(12) United States Patent
Caires Fernandez (10) Patent No.: US 9,790,153 B2
(45) Date of Patent: Oct. 17, 2017

(54) PROCESS SCHEME TO IMPROVE DIVALENT METAL SALTS REMOVAL FROM MONO ETHYLENE GLYCOL (MEG)

(75) Inventor: Luis Eduardo Caires Fernandez, Cypress, TX (US)

(73) Assignee: Cameron International Corporation, Houston, TX (US)

( * ) Notice: Subject to any disclaimer, the term of this patent is extended or adjusted under 35 U.S.C. 154(b) by 1235 days.

(21) Appl. No.: 13/295,666

(22) Filed: Nov. 14, 2011

(65) Prior Publication Data
US 2013/0118989 A1  May 16, 2013

(51) Int. Cl.
*B01D 21/01* (2006.01)
*C07C 29/76* (2006.01)
*B01D 9/00* (2006.01)
*B01D 3/06* (2006.01)

(52) U.S. Cl.
CPC ............ *C07C 29/76* (2013.01); *B01D 9/0009* (2013.01); *B01D 9/0054* (2013.01)

(58) Field of Classification Search
CPC ...................................................... B01D 3/40
See application file for complete search history.

(56) References Cited

U.S. PATENT DOCUMENTS

| 2,359,748 | A |  | 10/1944 | Clemens |  |
|---|---|---|---|---|---|
| 3,839,199 | A |  | 10/1974 | Weiss et al. |  |
| 4,017,391 | A |  | 4/1977 | Black |  |
| 4,059,513 | A |  | 11/1977 | Zadera |  |
| 4,209,395 | A |  | 6/1980 | Berlenbach et al. |  |
| 5,152,904 | A |  | 10/1992 | Kedem et al. |  |
| 5,518,633 | A |  | 5/1996 | Brown et al. |  |
| 5,683,587 | A |  | 11/1997 | Ferrara et al. |  |
| 6,340,373 | B1 | * | 1/2002 | Billington | ................ B01D 1/12 23/295 R |
| 6,425,942 | B1 | * | 7/2002 | Forster | ............... B01D 53/1425 95/174 |
| 6,444,095 | B1 | * | 9/2002 | Evans | ..................... C07C 41/42 159/17.1 |
| 6,627,085 | B2 |  | 9/2003 | Burrows et al. |  |

(Continued)

FOREIGN PATENT DOCUMENTS

NZ  2009000103 A1 * 12/2010
WO  2007073204  6/2007
(Continued)

*Primary Examiner* — Krishnan S Menon
*Assistant Examiner* — Ryan B Huang
(74) *Attorney, Agent, or Firm* — Gable Gotwals (57) ABSTRACT

A MEG reclamation process includes the step of increasing above 2,000 ppm the divalent metal salts concentration of a rich (wet) MEG feed stream flowing into a precipitator. The increasing step includes routing a salts-saturated MEG slipstream from the flash separator it to the precipitator. The slipstream may be mixed with a fresh water feed stream, a portion of the rich MEG feed stream, or some combination of the two. The rich MEG feed stream also may be split into two streams, with a portion of the stream being heated and routed to the flash separator and the other portion being combined as above with the removed slipstream. The process can be performed on the slipstream after dilution and prior to entering the precipitator or after being loaded into the precipitator. Removal of the insoluble salts may be done in either a batch or continuous mode.

17 Claims, 5 Drawing Sheets

(56) References Cited

U.S. PATENT DOCUMENTS

| | | |
|---|---|---|
| 6,919,031 B2 | 7/2005 | Blumenschein et al. |
| 7,083,730 B2 | 8/2006 | Davis |
| 7,232,505 B2 | 6/2007 | Laborie et al. |
| 7,718,069 B2 | 5/2010 | Laraway et al. |
| 7,815,804 B2 | 10/2010 | Nagghappan |
| 7,994,374 B2 * | 8/2011 | Talley .................. C10L 3/06 585/15 |
| 8,329,963 B2 * | 12/2012 | Chen ............................ 568/920 |
| 2003/0127391 A1 | 7/2003 | Craft, Sr. et al. |
| 2005/0072663 A1 * | 4/2005 | Laborie et al. ................. 203/18 |
| 2010/0191023 A1 * | 7/2010 | Chen ........................ C07C 29/88 568/920 |
| 2011/0094871 A1 * | 4/2011 | Nazzer ............................ 203/14 |

FOREIGN PATENT DOCUMENTS

| | | |
|---|---|---|
| WO | 2009017971 | 2/2009 |
| WO | WO 2009017971 A1 * | 2/2009 |
| WO | WO 2010080038 A1 * | 7/2010 |
| WO | WO 2011028131 A1 * | 3/2011 |

\* cited by examiner

PROCESS SCHEME TO IMPROVE DIVALENT METAL SALTS REMOVAL FROM MONO ETHYLENE GLYCOL (MEG)

BACKGROUND

This invention relates to processes designed to treat mono ethylene glycol (MEG) used in the oil and gas industry, especially in offshore locations, to control hydrates formation. More particularly, the invention relates to MEG reclamation processes which are designed to remove salts from a wet MEG feed stream.

In the oil and gas industry, dry (lean) MEG is used to control the formation of hydrates within the produced stream. The now wet (rich) MEG is, in turn, dried by way of a MEG reclamation process so the MEG can be used again in hydrate control. However, the lean MEG cannot be recovered by simply distilling the rich MEG and water because the rich MEG is commonly loaded with salts such as calcium chloride and, commonly, lesser amounts of other divalent metal salts like magnesium, barium and strontium chlorides. The salts have to be removed before the MEG and water are separated. If the salts are not removed prior to the MEG/water separation, the salts accumulate in the process equipment, eventually leading to process failure. This is especially problematic in processes whose design does not include a divalent metal salt removal step In processes that do include a divalent metal salt removal step, the divalent metal is usually removed by reacting it with precipitant agent such as sodium carbonate (soda ash), potassium carbonate or sodium oxalate. The resulting insoluble salt precipitates and is removed as solid crystals. Because the most common divalent metal present in rich MEG is calcium and the most common precipitating agent is sodium carbonate, the following descriptions are based on calcium removal as representative of divalent metals removal and sodium carbonate as representative of precipitating agents.

In a typical process having a calcium removal step, the calcium in the rich MEG will be reacted with sodium carbonate (soda ash) to form insoluble calcium carbonate and soluble sodium chloride. The insoluble calcium carbonate precipitates and is removed as solid crystals. The soluble sodium chloride remains in solution and is separated from the rich MEG by flashing the rich MEG under vacuum and at temperature. The vaporized water and MEG are then separated by partial condensation in what is commonly termed a "distillation" tower.

Flashing of the solvents (vaporized water and MEG) for the remaining salts (mostly sodium chloride) turns the salts into crystals that drop into a salt-saturated hot MEG solution which, in turn, is used as the heat transfer medium to drive the flashing process. Calcium presence in this step can promote severe viscosity problems and hinder proper settling of the newly formed crystals.

Calcium removal with soda ash treats the rich MEG stream at about 180° F. and needs about 15 minutes of residence time for the reaction to proceed and form reasonable size calcium carbonate crystals for decanting and removal. However, experiments conducted by the inventor have shown that calcium carbonate crystal growth, final size and reaction speed are normally favored by calcium chloride concentrations typically far above the concentration normally found in the rich MEG stream (usually less than 2,000 ppm). Lower concentrations of calcium in the precipitator inlet favor small size crystal formation, which in turn increases the difficulty of removal and residence time for the reactions to occur. The temperature requirement usually entails the use of heat exchangers to heat up the feed to the reaction temperature and may require more real estate than available, especially in offshore locations.

A need exists for a MEG reclamation process that removes calcium more effectively especially when the initial design did not include a calcium removal step (which is then found necessary later on) and intensifies the calcium removal process to make better use of limited space and existing equipment. Notwithstanding, the process can also be used for new designs to provide for a more compact divalent metal removal step than the current art.

SUMMARY OF THE INVENTION

A system for removing divalent metals from a monoethylene glycol ("MEG") feed stream includes treating with a precipitating agent a first MEG stream having a high concentration of divalent metal salts which exits a flash separator to induce divalent salt separation and precipitation in a precipitator sized to receive the first high divalent metal salts concentration MEG feed stream; and means for returning to the flash separator a second (now) lower divalent salts-saturated MEG stream exiting the precipitator.

A process (either continuous or batch) for removing divalent metal salts (especially calcium) from MEG as insoluble salts includes the steps of
  (i) increasing a divalent metal salts concentration of a MEG feed flowing into a precipitator so that the resulting divalent metal salts concentration of the MEG feed is above 2,000 ppm;
  (ii) treating the resulting divalent metal salts-concentration MEG feed in the precipitator with a precipitating agent;
  (iii) removing from the precipitator the insoluble salt formed and a divalent metal salts-saturated MEG stream;
  (iv) routing the removed divalent metal salts-saturated MEG stream into a flash separator.

In a preferred embodiment, the divalent metal is calcium and the increasing step increases the calcium concentration to about 25,000 ppm. The increasing step may include the sub-steps of removing a salt-saturated MEG slipstream from a liquid inventory of the flash separator and routing the removed slipstream to the precipitator. The removed slipstream may be mixed with a fresh water feed stream, a portion of the rich MEG feed stream, or some combination of the two. The mixed stream is then routed to the precipitator. Because of the way in which the process treats the increased calcium rich MEG feed stream, any sodium carbonate added to this stream prior to the precipitator is prevented from entering the flash separator.

The rich MEG feed stream may be split into two streams, with a portion of the stream being heated and routed to the flash separator and the other portion being combined as above with the removed slipstream. The removed slipstream may be cooled prior to it entering the precipitator. The fresh water feed stream or rich MEG feed stream (or some combination of the two) may be used to cool the slipstream.

Removal and processing of the slipstream from the flash separator may be done in either a batch mode or a continuous mode. When operating in a batch mode, the slipstream can be removed when the calcium concentration within the flash separator reaches a preset value (typically in a range of 40,000 to 50,000 ppm). In either mode, the calcium concentration within the separator should be kept below a plugging range (nearing the 60,000 ppm zone).

Objects of the invention are to (1) remove divalent metals such as calcium more effectively in less floor-space/volume when compared to current calcium removal processes without the need for additional specialized or new types of process equipment; (2) speed the reaction of calcium removal and promote larger-sized crystal formation by increasing the calcium ion concentration above 2,000 ppm of the feed entering the precipitator; (3) increase the velocity and conversion rate of the calcium removal reaction by increasing the feed temperature entering the precipitator via direct mixing with the fresh feed or water; (4) prevent the release of carbon dioxide by avoiding the introduction of soluble precipitating agents into the elevated temperature flash separator or separator; and (5) reduce MEG losses significantly by minimizing the MEG content contained in the disposed salts. In the case of calcium carbonate, direct mixing with fresh feed or water reduces the solubility of the calcium carbonate and favors higher conversion of calcium chloride into calcium carbonate. Higher conversion is achieved because the carbonate precipitates to a greater extent to reach the lower equilibrium concentration at the higher temperature.

BRIEF DESCRIPTION OF THE DRAWINGS

FIG. 1 shows a schematic of a prior art process that considers the presence of calcium in the feed. The low calcium concentration (typically less than 2,000 ppm) of the wet MEG, fresh feed stream is heated and mixed with sodium carbonate. The mixture enters a precipitator where the calcium carbonate forms and precipitates. The precipitation process removes calcium from the stream and the salt-saturated MEG stream is further heated and routed to a flash drum or separator. In the flash separator, the water and most of the MEG are flashed off to be distilled downstream. Sodium chloride is removed as crystals from the bottom of the flash separator.

FIG. 2 shows a schematic of a prior art process that does not properly consider the presence of calcium in the rich MEG feed stream. Therefore, calcium in the feed stream accumulates in the flash separator and impairs sodium chloride removal. Calcium accumulation in the flash separator may also lead to severe salt deposition and plugging. Operators may be forced to dump MEG from the flash separator and replace it with fresh MEG to purge calcium or lower its concentration in the flash separator. For an existing facility, it may not be feasible to turn the process shown in FIG. 2 into that of FIG. 1, with a full-fledged precipitator and preheating system. Additionally, the low calcium concentration in the rich MEG feed stream may lead to requiring a precipitator much larger in size than current space constraints can accommodate.

ELEMENTS AND NUMBERING USED IN THE DRAWINGS AND THE DETAILED DESCRIPTION

10 MEG reclamation process with calcium removal
20 Fresh, wet (rich) MEG feed stream
22 Heating medium
24 Pre-Heated fresh feed stream
26 Precipitator feed stream
28 Precipitating agent
30 Fresh water feed stream
32 Fresh feed/fresh water stream
34 Diluted slipstream
40 Precipitator
42 Calcium carbonate stream
43 Recycle loop
44 Calcium salts-saturated MEG stream
46 Heating medium
48 Heated calcium salts-saturated MEG stream
50 Flash separator stream
60 Flash drum or separator
62 Slipstream
64 Salt crystal outlet stream
66 Vaporized water and MEG stream
68 Heat transfer medium

DETAILED DESCRIPTION OF THE PREFERRED EMBODIMENTS

Figure 3:
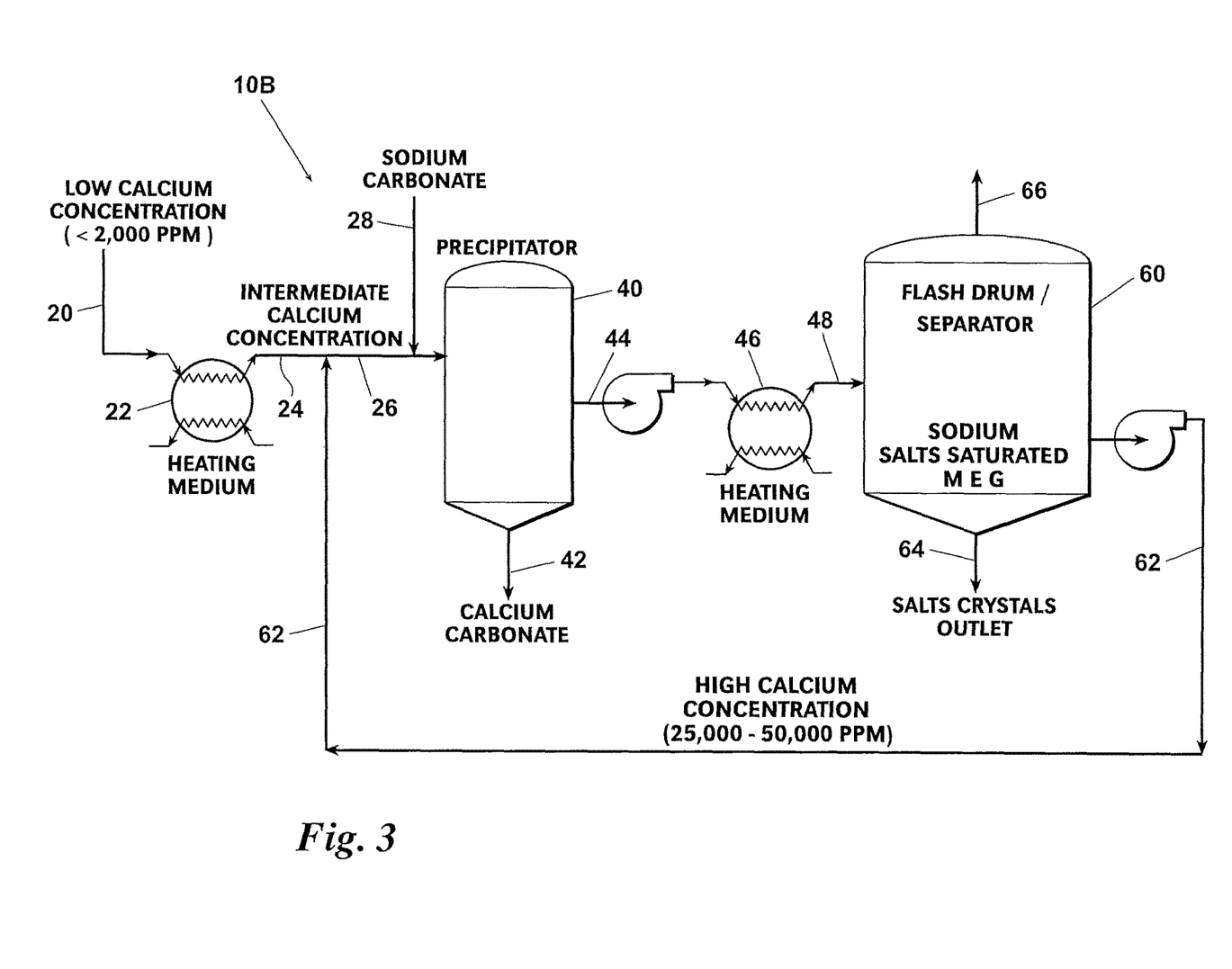
FIG. 3 shows a preferred embodiment of a MEG reclamation process practiced according to this invention. The process removes calcium from a rich MEG feed stream by using smaller equipment than the process of FIG. 1 and effectively removes accumulated calcium from the flash separator.

Referring first to FIG. 3, a preferred embodiment of a MEG reclamation process 10A practiced according to this invention begins with a fresh, wet (rich) MEG feed stream 20 which is then heated by way of a heating medium 22 to form a pre-heated fresh feed stream 24. Fresh feed stream 20 is typically low in calcium concentration (less than 2,000 ppm). The pre-heated fresh feed stream 24 is mixed with a slipstream 62 that has been removed from a liquid inventory of a flash drum or separator 60 to form a precipitator feed stream 26. A precipitating agent 28, preferably sodium carbonate, is added to the precipitator feed stream 26.

Figure 1:
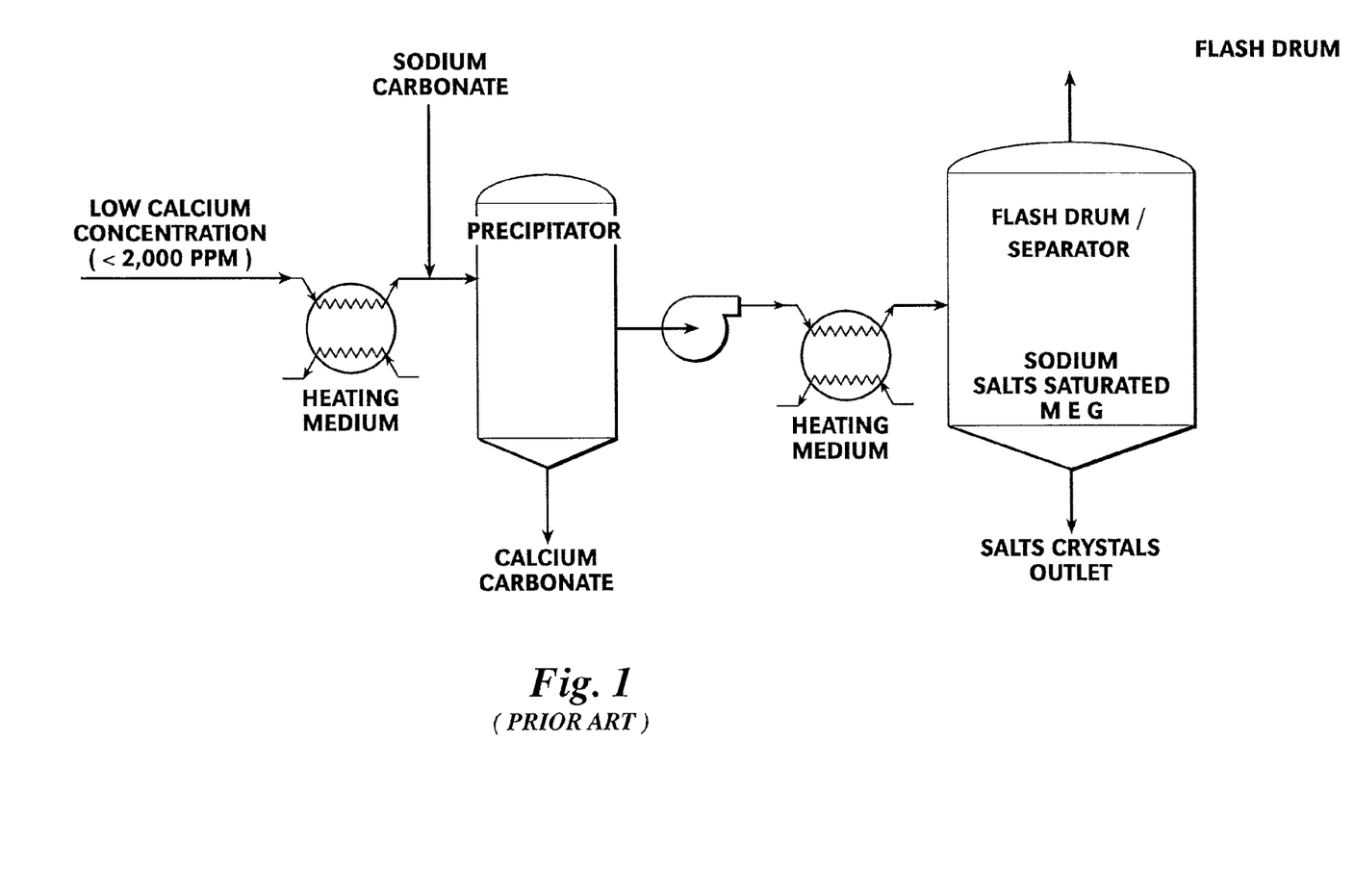
Figure 2:
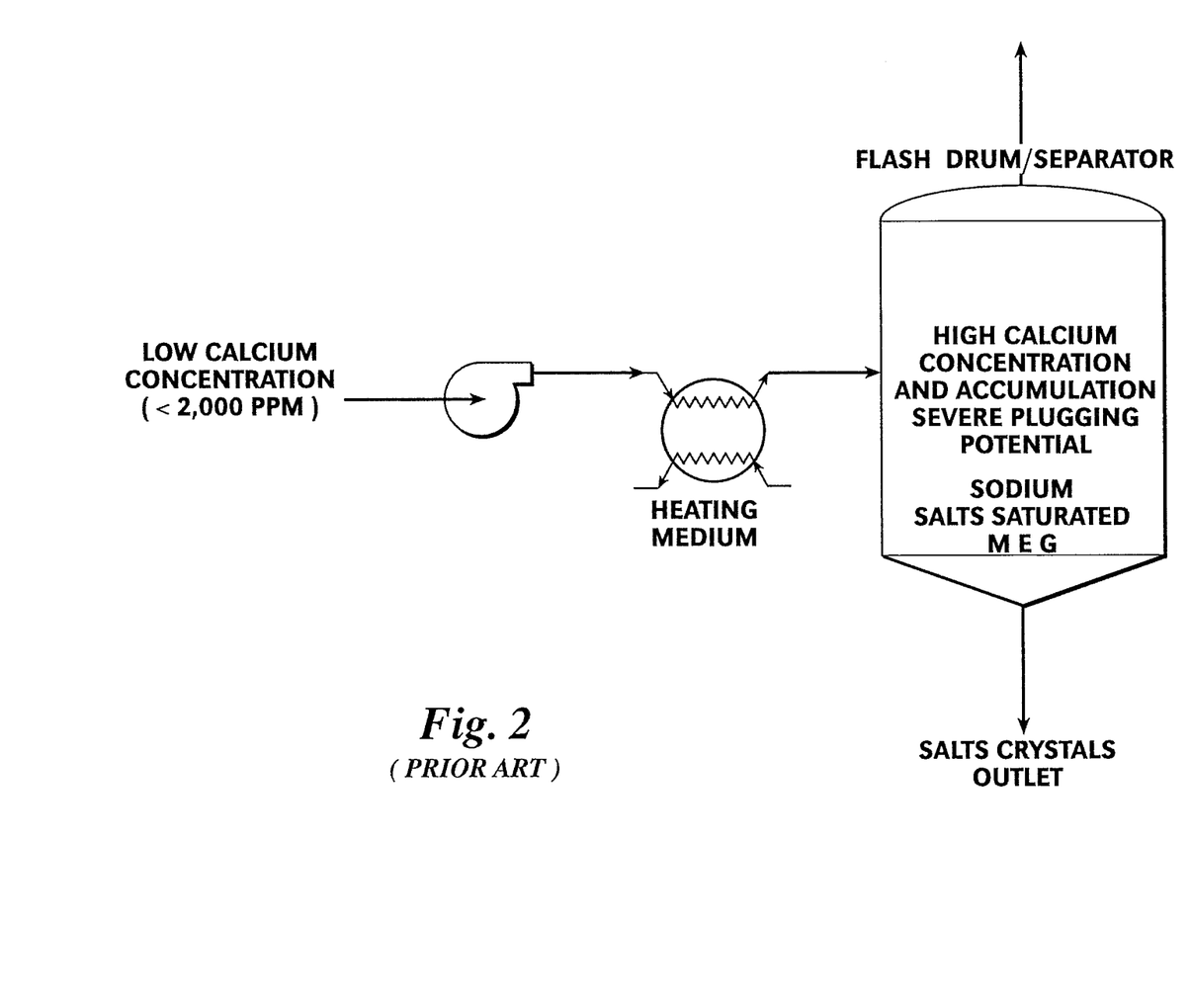

Mixing slipstream 62 with the pre-heated fresh feed stream 24 increases the calcium concentration of the precipitator feed stream 26 above that of initial fresh feed stream 20 but below that of slipstream 62. In general terms, the calcium concentration of precipitator feed stream 26 is in a range of about 10,000 to 30,000 ppm. However, the exact calcium concentration of the stream 26 depends upon the flow rate and calcium concentration of the pre-heated fresh feed stream 24 and the slipstream 62 (which may be in a range of about 25,000 to 50,000 ppm). Slipstream 62 increases the temperature of the precipitator feed stream 26 because the flash separator 60 operates at higher temperature than does the precipitator 40. This allows the heating medium 22 to be reduced in size compared to prior art processes (see e.g. FIG. 1) and yet still meet the desired temperature for precipitator feed stream 26.

A calcium carbonate stream 42 exits a bottom end of precipitator 40 and a calcium salts-saturated MEG stream 44 exits a top end. The calcium salts-saturated MEG stream 44 is heated by a flash separator heater 46 and the heated calcium salts-saturated MEG stream 48 is routed into flash separator 60. A salt crystals stream 64 exits a bottom end of flash separator 60 and a vaporized water and MEG stream 66 exits a top end. The water and MEG components of the vaporized water and MEG stream 66 are then separated from one another by partial condensation in what is commonly termed a "distillation" tower (not shown).

To maintain a constant residence time in precipitator 40, a person of ordinary skill in the art would recognize the volume of the precipitator 40 must increase linearly with the total flow of precipitator feed stream 26. However, because the precipitation reaction is basically a second order one in calcium concentration, the effect of the increase in overall calcium concentration in the precipitator feed stream 26 (in most cases) more than offsets the need for increased residence time. Therefore, the same conversion of calcium removal can be reached now with less residence time compared to prior art processes.

The size/volume of precipitator 40, the flow rate of the pre-heated fresh feed stream 24, the recirculation flow rate of the slipstream 62, and the heat exchange of the heated calcium salts-saturated MEG steam 48 are preferably designed so that the steady state calcium concentration in the flash separator 60 is maintained below the severe plugging range (typically in the range of 50,000 to 60,000 ppm). The removal of slipstream 62 from flash separator 60 may be operated in a batch mode, drawing the slipstream 62 from the flash separator 60 when the overall calcium concentration within the flash separator 60 reaches a preset but safe high value.

Figure 4:
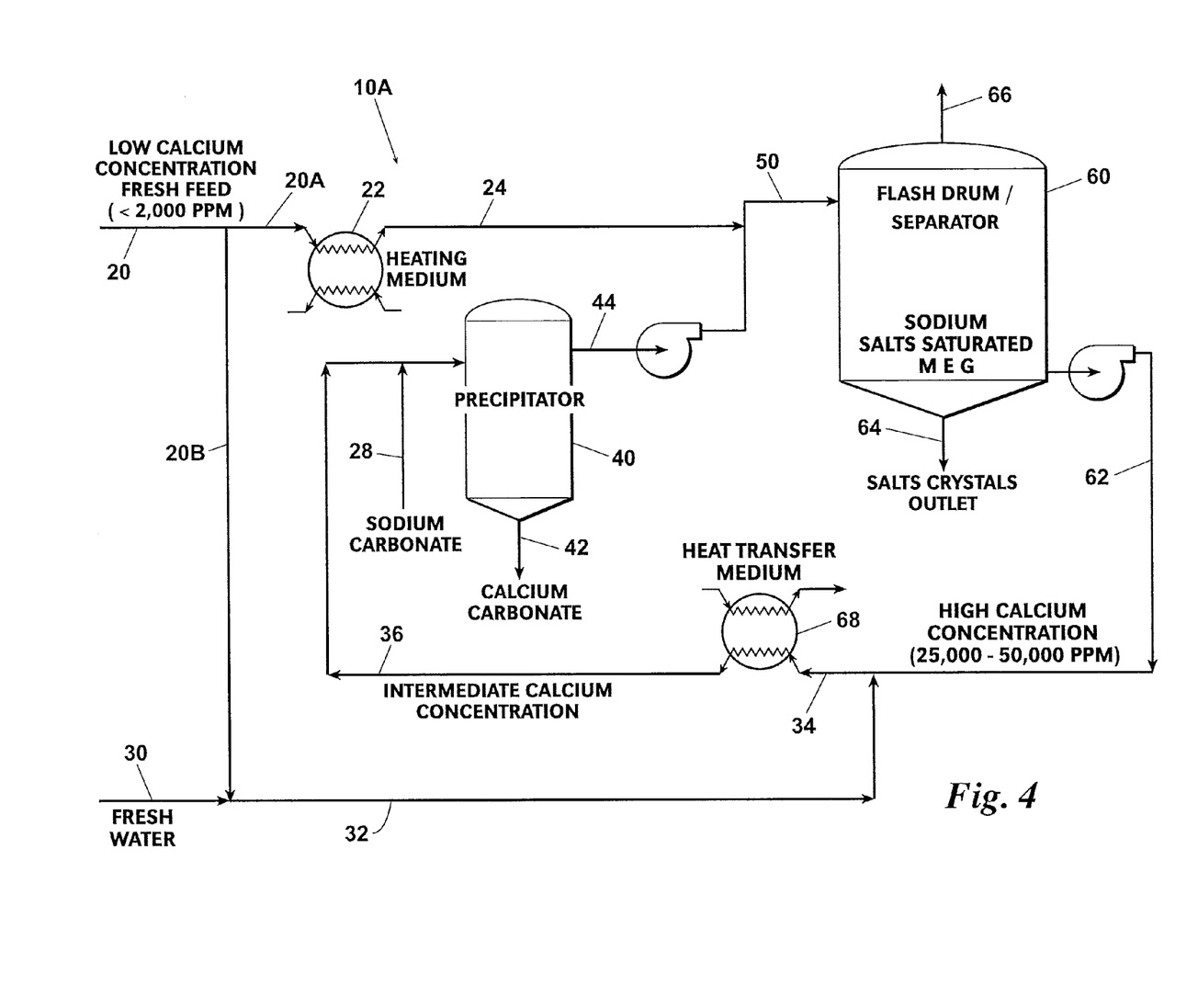
FIG. 4 presents another preferred embodiment of a MEG reclamation process practiced according to this invention in which the same concepts as those of FIG. 3 are used.

Referring now to FIG. 4, another preferred embodiment of a MEG reclamation process 10B practiced according to this invention is illustrated. In this embodiment, fresh, wet (rich) MEG feed stream 20 is split into two fresh feed streams 20A, 20B, with fresh feed stream 20A being heated by heating medium 22 to produce a pre-heated fresh feed stream 24 which is combined the salt-saturated MEG stream 44 exiting precipitator 40 to form flash separator stream 50. Flash separator stream 50 is then routed to flash separator 60. A calcium carbonate stream 42 exits a bottom end of precipitator 40 and a salt-saturated MEG stream 44 exits a top end.

Fresh feed stream 20B combines with slipstream 62 from the flash separator 60 to form precipitator feed stream 36. Unlike process 10A of FIG. 3, in process 10B slipstream 62 is partially diluted (to avoid crystallization upon cooling and improve heat transfer) with fresh feed stream 20B and fresh water stream 30 to form fresh feed/flesh water stream 32. The high concentration calcium slipstream 62 is then combined with fresh feed/fresh water stream 32 to form a diluted slipstream 34 whose temperature is further adjusted by the heat transfer medium 68 (cooling or heating depending on the specifics of the design situation) so that the resulting precipitator feed stream 36 is at the required precipitator temperature. The dilution and temperature adjustment of slipstream 62 could be provided by the fresh feed 20B itself but whether this is best or desired in any given application depends upon available utilities and other practical considerations. The removal of slipstream 62 can be operated in batch or continuous mode as previously described.

Figure 5:
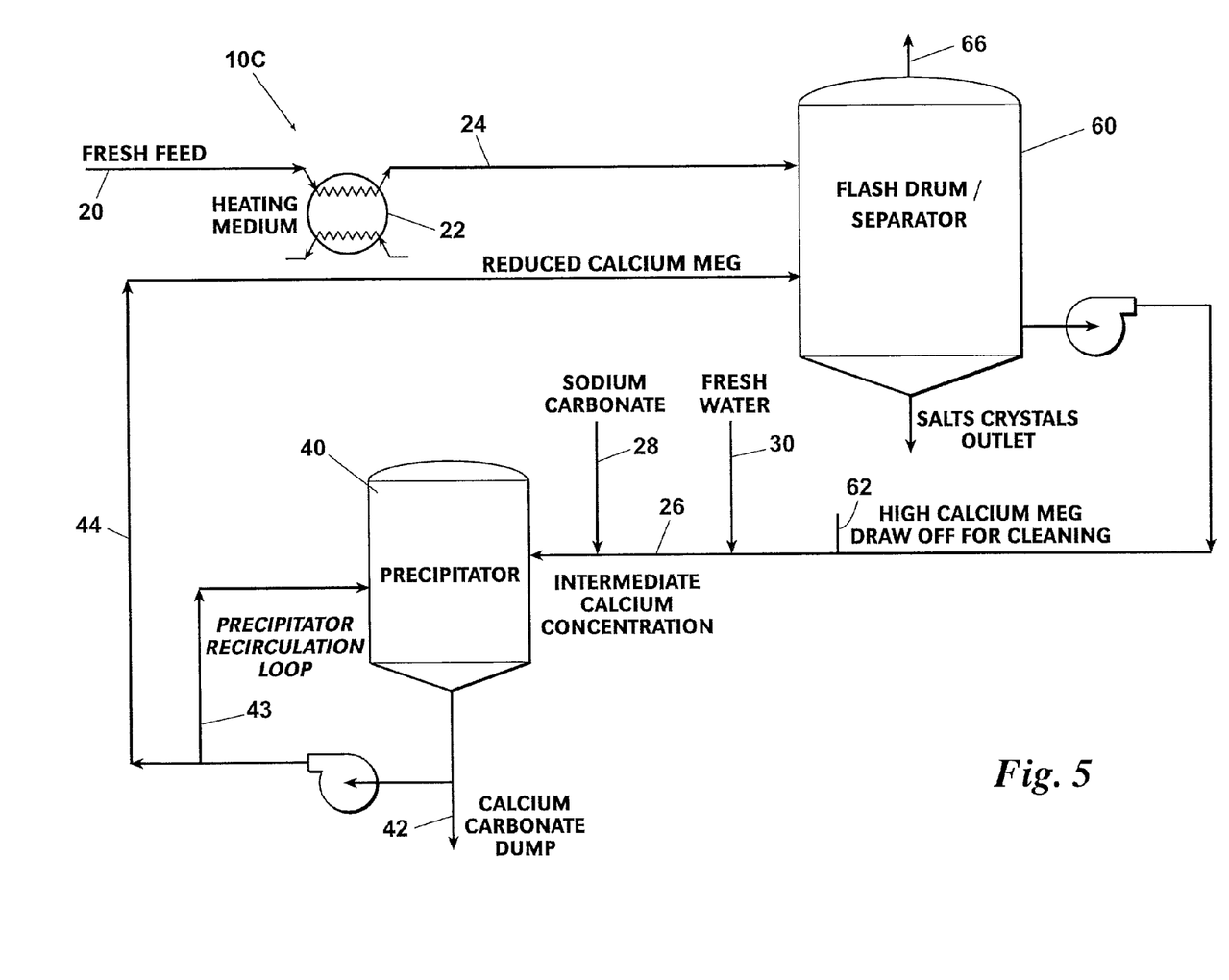
FIG. 5 presents another embodiment of the MEG reclamation process suitable for operating in a batch mode using the same concepts as those of FIGS. 3 and 4.

Referring now to FIG. 5, another preferred embodiment of a MEG reclamation process 10C is illustrated which is very well suited for batch calcium removal applications, even though it can also operate in a continuous mode. The batch removal process is described herein.

Fresh feed 20 is heated with a heating medium 22 and the resulting preheated fresh feed stream 24 is flashed in the flash separator 60. The soluble calcium salts accumulate in the flash separator 60 until reaching a high calcium concentrate trigger point (preferably within a range of 25,000 to 50,000 ppm).

Upon reaching the calcium concentration trigger point, a slip stream 62 is taken from the flash separator 60 and preferably mixed with sodium carbonate 28 (the precipitating agent) to become the precipitator feed stream 26. The flows are kept until the batch to be treated is loaded into the precipitator 40 to start the precipitation reaction phase. After the precipitator 40 is loaded, the fluids in the precipitator 40 are allowed to react and form the calcium carbonate crystals. The fluids may be re-circulated in a recycle loop 43 (as depicted) or otherwise stirred to promote good contact of the calcium chloride and the sodium carbonate to form the calcium carbonate crystals. Reaction times will usually be such total batch treatment can be completed with an 8-hour work shift.

At the completion of the precipitation reaction phase, the solids 42 are removed from the precipitator 40 and the (now) lower calcium-salts saturated MEG stream 44 is returned to the flash separator 60. The solid separation is not limited to decanting because separation can be enhanced by using centrifuges or other types of solid/liquid separators.

While preferred embodiments of a MEG reclamation system and process have been described in detail, a person of ordinary skill in the art understands that certain changes can be made in the arrangement of process steps and type of components used in the process without departing from the scope of the following claims.

What is claimed is:

1. A process for removing divalent metals from a rich mono-ethylene glycol ("MEG") feed stream, the process comprising:
   removing a salt-saturated MEG stream from a liquid inventory of a flash separator;
   routing a rich MEG feed stream to a precipitator upstream of the flash separator;
   increasing a divalent metal salts concentration of the rich MEG feed stream by adding to the rich MEG feed stream the removed salt-saturated MEG stream recycled from the flash separator before the rich MEG feed stream enters the precipitator;
   chemically reacting the increased divalent metal salt concentrated rich MEG feed stream with a precipitating agent so that insoluble salts are formed at precipitator operating conditions;
   removing an insoluble salts stream from the precipitator; and
   removing a divalent metal salts-saturated MEG stream from the precipitator; and
   routing the divalent metal salts-saturated MEG stream into the flash separator.

2. A process according to claim 1 wherein the removed salt-saturated MEG stream is diluted before entering the precipitator to adjust at least one of a precipitator feed and a divalent salts concentration.

3. A process according to claim 1 further comprising mixing the removed salt-saturated MEG stream with at least one of a fresh water feed stream and a first portion of the rich MEG feed stream.

4. A process according to claim 1 further comprising:
   splitting the rich MEG feed stream into a first portion and a second portion;
   heating the second portion of the rich MEG feed stream; and
   routing the heated second portion to the flash separator.

5. A process according to claim 4 further comprising the heating step occurring before the increasing step and mixing the heated second portion with the divalent metal salts-saturated MEG stream.

6. A process according to claim 1 further comprising adjusting the temperature of the removed salt-saturated MEG stream prior to the removed salt-saturated MEG stream entering the precipitator.

7. A process according to claim 1 further comprising the removing step from the flash separator being operated in a batch mode.

8. A process according to claim 7 wherein the removing step from the flash separator occurs when a divalent metal salts concentration within the flash separator reaches a preset value.

9. A process according to claim 1 further comprising the removing step from the flash separator being operated in a continuous mode.

10. A process according to claim 1 further comprising the increasing step increasing the divalent metal salts concentration to about 25,000 ppm.

11. A process according to claim 1 further comprising maintaining a divalent metal salts concentration in the flash separator below 60,000 ppm.

12. A process according to claim 11 wherein the divalent metal salts concentration is in a range of 30,000 to 50,000 ppm.

13. A process according to claim 1 further comprising preventing the precipitating agent from entering the flash separator by the step of using the precipitating agent as a limiting reactant.

14. A process according to claim 1 further comprising the increasing step including:
cooling the increased divalent metal salt concentrated rich MEG feed stream.

15. A process according to claim 1 further comprising the increasing step including heating the increased divalent metal salt concentrated rich MEG feed stream.

16. A process for removing divalent metals from a rich mono-ethylene glycol ("MEG") feed stream, the process comprising:
removing a salt-saturated MEG stream from a liquid inventory of a flash separator;
routing the removed salt-saturated MEG stream into a precipitator upstream of the flash separator;
chemically reacting the removed salt-saturated MEG stream in the precipitator with a precipitating agent so that insoluble salts are formed at precipitator operating conditions;
removing an insoluble salts stream from the precipitator; and
removing a lower salt-saturated MEG stream from the precipitator, the lower salt-saturated MEG stream having a lower salt concentration than the salt-saturated MEG stream removed from the liquid inventory of the flash separator; and
routing the removed lower salt-saturated MEG stream into the flash separator.

17. A process for removing divalent metals from a rich mono-ethylene glycol ("MEG") feed stream, the process comprising:
increasing a divalent metal salts concentration of a rich MEG feed stream when the rich MEG feed stream enters a precipitator vessel by adding to the rich MEG feed stream a salt-saturated MEG stream removed from a downstream flash separator arranged to receive a lean MEG stream exiting the precipitator vessel.

* * * * *